United States Patent
Dhar et al.

(10) Patent No.: US 7,087,389 B2
(45) Date of Patent: Aug. 8, 2006

(54) HIGHLY COST-EFFECTIVE ANALYTICAL DEVICE FOR PERFORMING IMMUNOASSAYS WITH ULTRA HIGH SENSITIVITY

(75) Inventors: Tarun K. Dhar, Calcutta (IN); Arindam Pal, Calcutta (IN)

(73) Assignees: Council of Scientific & Industrial Research, New Delhi (IN); Department of Biotechnology, A Department of Govenment of India, New Delhi (IN)

( * ) Notice: Subject to any disclaimer, the term of this patent is extended or adjusted under 35 U.S.C. 154(b) by 0 days.

(21) Appl. No.: 09/779,455

(22) Filed: Feb. 9, 2001

(65) Prior Publication Data

US 2002/0110803 A1    Aug. 15, 2002

(51) Int. Cl.
*G01N 33/53* (2006.01)
(52) U.S. Cl. .................... 435/7.1; 422/56; 422/60; 422/61; 435/287.7; 435/287.8; 435/287.9; 435/288.3; 435/7.1; 436/518; 436/524; 436/530; 436/541; 436/809; 436/810; 436/823
(58) Field of Classification Search .............. 422/56, 422/60, 61; 435/287.7, 287.8, 287.9, 288.3; 436/518, 524, 530, 541, 809, 810, 823
See application file for complete search history.

(56) References Cited

U.S. PATENT DOCUMENTS

| | | | |
|---|---|---|---|
| 4,233,029 A | | 11/1980 | Columbus |
| 4,235,601 A | * | 11/1980 | Deutsch et al. |
| 4,246,339 A | * | 1/1981 | Cole et al. |
| 4,310,399 A | | 1/1982 | Columbus |
| 4,366,241 A | | 12/1982 | Tom et al. |
| 4,426,451 A | | 1/1984 | Columbus |
| 4,446,232 A | | 5/1984 | Liotta |
| 4,518,565 A | * | 5/1985 | Boger et al. |

(Continued)

FOREIGN PATENT DOCUMENTS

GB    2342443 A   *  12/2000

OTHER PUBLICATIONS

Bhattacharya, R. et al. "A novel signal amplification technology based on catalyzed reporter deposition and its application Dot-ELISA with ultra high sensitivity," J Immunol. Methods, Jul. 30, 1999, 227:31-39, Elsevier Science B.V.

(Continued)

*Primary Examiner*—Bao-Thuy L. Nguyen
(74) *Attorney, Agent, or Firm*—Foley & Lardner LLP

(57) ABSTRACT

A simple easy to manufacture analytical device capable of performing membrane based immunoassays on batch of samples within 3 to 10 minutes wherein the method permits focused application of samples, costly labeled immunoassay and signal amplification reagents, said device includes an antibody-immobilized micro porous membrane, breadth corner layer of which is directly attached to a semi-rigid liquid-impervious body with water insoluble adhesive; absorbent body is provided separately and is not attached to analytical device during manufacture, absorbent body is wetted and is placed proximal to the lower surface of the membrane thereby forming networks of capillary channels with the absorbent body; flow of samples or reagents is always kept downwards and focused without application of any force to the absorbent body and the use of disposable adsorbent body permits stepwise addition of signal amplification reagents for ultra sensitive detection of diagnostically important molecules by visual examination of the membrane surface.

18 Claims, 5 Drawing Sheets

U.S. PATENT DOCUMENTS

| | | | |
|---|---|---|---|
| 4,632,901 A | | 12/1986 | Valkirs et al. |
| 4,727,019 A | | 2/1988 | Valkirs et al. |
| 4,727,037 A | * | 2/1988 | Ring |
| 4,818,677 A | | 4/1989 | Hay-Kaufman |
| 4,990,442 A | * | 2/1991 | Del Campo |
| 5,019,347 A | * | 5/1991 | Hiratsuka et al. |
| 5,059,522 A | * | 10/1991 | Wayne |
| 5,098,846 A | * | 3/1992 | Fleming |
| 5,202,432 A | * | 4/1993 | Del Campo |
| 5,270,167 A | * | 12/1993 | Francoeur |
| 5,486,452 A | * | 1/1996 | Gordon et al. |
| 5,569,589 A | * | 10/1996 | Hiraoka et al. |
| 5,573,919 A | * | 11/1996 | Kearns et al. |
| 5,807,522 A | * | 9/1998 | Brown et al. |
| 5,885,526 A | | 3/1999 | Chu |
| 5,922,615 A | | 7/1999 | Nowakowski et al. |
| 6,045,753 A | * | 4/2000 | Loewy et al. |
| 6,265,176 B1 | * | 7/2001 | Lin et al. |
| 6,372,515 B1 | * | 4/2002 | Casterlin et al. |
| 6,406,922 B1 | * | 6/2002 | Casterlin et al. |
| 6,514,769 B1 | * | 2/2003 | Lee |

OTHER PUBLICATIONS

Bhattacharya, D. et al. "A novel signal amplification technology based on catalyzed reporter deposition. Demonstration of its applicability for measuring aflatoxin $B_1$," J Immunol. Methods, 1999, 230:71-86, Elsevier Science B.V.

Bobrow, M. et al. "Catalyzed reporter deposition, a novel method of signal amplification. II. Application to membrane immunoassays," J. Immunol. Methods, 1991, 137:103-112, Elsevier Science Publishers B.V.

Bobrow, M. et al. "Catalyzed reporter deposition, a novel method of signal amplification," J. Immunol. Methods, 1989, 125:279, Elsevier Science Publishers B.V.

Porstmann, T. et al. "Enzyme immunoassay techniques—An overview" J. Immunol. Methods, 1992; 150: 5-21, Elsevier Science Publishers B.V.

Bates, D.L. "Enzyme amplification in diagnostics", Trends in Biotechnology, 1987, 5:204-209, Elsevier Publications.

Hawkes, R. et al. "A Dot-Immunobinding Assay for Monoclonal and Other Antibodies", Analytical Biochemistry, 1982, 119:142-147, Academic Press, Inc.

\* cited by examiner

HIGHLY COST-EFFECTIVE ANALYTICAL DEVICE FOR PERFORMING IMMUNOASSAYS WITH ULTRA HIGH SENSITIVITY

FIELD OF THE INVENTION

The present invention relates to analytical device and methods for use in determining analyte in batch of sample suspected of containing such analyte with ultra high sensitivity. More particularly, the invention relates to device and simple methods for application of signal amplification reagents after immunoassay in a laboratory or a field setting for attaining high sensitivity.

BACKGROUND AND PRIOR ART INVENTION

The diagnostically important molecules may be small molecules or macromolecules. The small molecules like mycotoxins such as aflatoxin $B_1$, Ochratoxin A T-2 toxin are present in food and feed such as cereal grains, ground nuts, rice, peanuts, fodder as contaminants due to fungal infection. Human and animals are exposed to mycotoxins through ingestion of toxin-contaminated food and feed, inhalation or skin contact. The determination of mycotoxins in agricultural commodities is important because their consumption by man and animals causes mycotoxicosis. They also produce different biological effects such as acute toxicity, mutagenicity, carcinogenicity, tertogenicity etc (Morgan, M. R. A. *Tetrahedron* 45, 2237, 1989). The determination of the concentration of steroids such as estriol, dehydroepiandrosterone sulphate, cortisol, testosterone, hormones such as thyroxin, triiodothyronine and drugs such as methoxtrate present in biological fluid such as serum, plasma, urine in minute amounts have been accepted as one of the attractive indicators of several diseases and in pathological conditions (Methods of Hormone Radioimmunoassay Ed. Jaffe, B. M. and Behrman, H. R. 1979, Academic Press, New York).

The diagnostically important macromolecules like hormones such as thyroid stimulating hormones (TSH), adrenocortcotropic hormone (ACTH) or cancer markers such as acid phosphatase, ferritin, carcinoembroynic antigen are present in biological fluid such as serum, plasma in extremely minute amounts. These biologically important molecules have been widely accepted as the effective indicators of disease. Similarly, diagnosis of various infectious diseases also require detection of antigen such as hepatitis, malaria or detection of antibodies in cases of diseases like AIDS, amoebiosis (Methods of Enzymatic Analysis, Ed. By Bergmeyer, J. and Gross, vol. X, XI, 1983, Verlag chemie, Weinheim). These antigen or antibodies are present in biological fluid such as serum in extremely minute amounts and early detection sometimes is not possible. Some of these infectious diseases are detected by the present available methods only at a later stage when the concentration of antigen or antibody in biological fluid is increased.

Detection of these diagnostically important molecules requires highly sensitive assay system. Immunological assays have proven to be of great value for detection and quantification of numerous analytes in liquid samples. Because the results of immunological and other specific binding reactions are frequently not directly observable, various techniques have been devised for their indirect observation. Such techniques involve labeling of one of the members of the specific binding pair with a radioisotope, chromophore, fluorophore or enzyme label. Radiolabels, chromophores and fluorophores may be detected by the use of radiation detectors, spectrophotometers. Where members of a specific binding pair are tagged with an enzyme label, their presence may be detected by the enzymatic activation of a reaction system wherein a compound such as a dyestuff, is activated to produce a detectable signal. Such procedures are described in a number of articles and texts, an example of which is *Reviews on Immunoassay Technology*, Ed. S. B. Pal, Pub. Chapman and Hall, 1988.

Among the different immunoassays, enzyme labels tagged with specific binding pair are widely used. These assays are called enzyme immunoassay, commonly termed as ELISA. At present for small molecules competitive ELISA and for macromolecules sandwich ELISA method is widely used for their determination (Porstman, T. and Kiessig, S. T. *Journal Immunological Methods* 150, 5, 1992)

In competitive ELISA, sample or standard is added to a solid phase such as 96-well microtitre plate, tubes, beads coated with an antibody raised against small molecules to be determined. They are incubated after the addition of an enzyme, which is covalently linked with the small molecule at a temperature in the range of 4° C. to 37° C. for a period of 2 to 24 hrs. The analyte to be detected competes with a labeled reagent of the same analyte for a limited number of antibody binding sites. The amount of labeled antigen, which binds to the antibody, is inversely proportional to the amount of the unknown antigen in the sample.

The solid phases are washed with a buffer and substrate solution is added which gives colour due to the enzymatic activity of the enzyme conjugate bound to the antibody immobilized over solid phase. The intensity of the colour is inversely proportional to the concentration of small molecule present in the sample. Visualization of the intensity of the colour with naked eye in comparison with known concentration of small molecule gives an idea about the relative amount of small molecule present in the sample. The amount of colour developed may also be measured for quantitative determination by spectrophotometer or automatic microtitre plate reader. The measured absorbances are plotted against known concentration of small molecule to obtain a standard curve. Concentration of small molecule in samples is calculated from this standard curve by standard procedure.

In another assay, known as sandwich ELISA method, a solid surface such as 96-well microtitre plate, tubes are coated with monoclonal antibody obtained against macromolecules to be determined. Vacant sites are blocked with blocking protein such as casein, BSA. Standards or samples containing macromolecules are added to solid phase and incubated at a temperature in the range of 4 to 37° C. for a period of 2 to 24 hrs. The selected macromolecular antigen in the sample or standard binds to the receptor monoclonal antibody. The solid phase is washed and further incubated for a period of 2 to 24 hrs with a second polyclonal antibody (against macromolecules) covalently linked with an enzyme which is capable of binding to the bound antigen to form an immobilized reaction product. The solid phase is further washed. The label in the reaction product is detected which indicates the presence of the antigen in the sample. The concentration of macromolecule in samples is determined as described in above method.

These immunological detection methods as described above are widely used for detection of biologically important molecules commonly referred to as analytes. These methods are simple but have following drawbacks:

1. They require well-equipped laboratories and are designed for testing samples in batches.

2. The presence of mostly long incubation period makes the method elongated and time consuming.
3. The detection limit of the method is low, making the detection of analytes present in extremely minute amount very difficult.
4. These assays are not suitable for on-site testing or for use under field conditions.

Dot-immunobinding assays introduced as an alternative to ELISA for detection of antigen or antibody (Hawkes, R., et. al. *Analytical Biochemistry* 119, 142, 1982) have brought a great revolution in the field of diagnostic. These methods commonly referred to as membrane-based assays are similar to ELISA and only difference is that here membrane are used as immunosorbent instead of microtitre plate or tubes. They also have competitive methods for small molecules and non-competitive or sandwich methods for macromolecules. Here monoclonal antibody that is capable of specifically binding to the target substance is immobilized over the membrane. In the assay, the sample to be tested is applied to the reaction membrane. If the target analyte is present in the sample, it will bind to the immobilized receptor. Typically after incubation step the sample was separated from the solid phase, which was then washed and incubated with a solution of additional polyclonal antibodies covalently, labeled with enzyme. After incubation, the unbound-labeled antibody was separated from the solid phase and the amount of labeled antibody bound to the solid phase was determined. These methods are simple, colour is visible over white background of the membrane. The method has following drawbacks:
1. The detection limit of the method is low and is in the range of 500 to 2000 pg making the detection of antigen or antibody in test samples difficult.
2. The long incubation period makes the method time consuming.
3. The low detection limit of the method has limited its application for detection of antigen or antibody, which are present in extremely minute amount.
4. Membranes are delicate in nature and their handling becomes difficult.

Detection of analyte present in low concentration requires sample concentration or longer incubation time to generate sufficient signal for accurate estimation of analytes. However, because of the low sensitivity of membrane-based assays and non-specific interference, interpretation of the results may not be accurate. Application of enzyme amplification step has been proved to be very efficient in not only increasing the sensitivity but also reducing the assay time (Bates, *Trends in Biotechnology*. 5, 204,1987). In these procedures, the solid phase bound primary enzyme is linked catalytically to an additional system, which not only amplifies the signal but also increases the sensitivity.

Bobrow et al., (*Journal of Immunological Methods,* 125, 279, 1989; *Ibid.* 137, 103, 1991) described a signal amplification system called 'Catalyze Reporter Deposition' (CARD) method to improve detection limit in immunoassays using rabbit IgG as test analyte. In this method, diluted solution of antigen (rabbit IgG) at different concentration was applied over nitrocellulose membrane strip as dots. It was dried, blocked with 5% casein and incubated with double antibody-peroxidase conjugate. It was again incubated with biotin-tyramine conjugate containing 0.004% hydrogen peroxide. Membrane bound peroxidase catalyzes phenolic portion of biotin-tyramine conjugate which deposits on to the surface of membrane. The deposited biotin is then reacted with streptavidin labeled enzyme thereby resulting in deposition of enzymes. The net effect is that a single HRP label is surrounded by many peroxidase molecules. The membrane is incubated with substrate solution and due to enzymatic activity colour develops over the membrane as dots. The intensity of colour is directly proportional to the amount of colour developed. The method also called 'Tyramide Signal Amplification' is flexible and can be applied as an additional step after conventional Dot-ELISA. In this method, due to deposition of additional enzyme results in amplification and thereby improving the detection limit by more than 25-fold. However, this method has following disadvantages:
1. The detection limit of the method with different substrate solution depending on the enzyme label used for streptavidin is in the range of 80 to 1 pg.
2. The increased in sensitivity is only 30-fold.
3. Long incubation periods required makes the method time consuming.

Recently, the applicants have developed a novel signal amplification method based on catalyzed reporter deposition. The method termed Super-CARD method utilizes synthesized electron rich proteins having multiple copies of phenolic group as blocking agents. After completion of conventional assay, the solid phase bound HRP oxidises the added labeled substrate, which deposits onto the solid phase. This deposition is markedly increased in the presence of immobilized electron rich proteins, which not only amplifies the signal but also increases the sensitivity. The high specificity of the amplification reaction avoids the generation of any false positive signal. Direct comparison with existing CARD methods demonstrates approximately $1.6 \times 10^4$-fold enhancement in detection sensitivity which is much higher than that of any other existing methods (Indian Pat. No. 1996/DEL/97; 1989/DEL/97; 1991/DEL/97 and published in *Journal of Immunological Methods* 227, 31–39, 1999; *Ibid.* 230, 71–86, 1999). The method offers several advantages:
1. The method is simple and easy to implement.
2. The novel protein conjugates used as blocking agents can be prepared from commercially available inexpensive proteins and chemicals.
3. The same reagents used in CARD amplification can be used.

As the membranes are very delicate and difficult to handle, numerous assay devices, in various configurations were developed for wider use under field conditions. The dipstick was first to be introduced, generally uses a plastic strip with membrane containing immobilized antibody attached at one end for dipping into a solution either containing or suspected of containing the analyte of interest. When incubated, analyte present in the sample binds to antibody immobilized over membrane. The extent to which the analyte becomes bound to that zone can be determined with the aid of labeled reagents. Typically, the user determines the concentration of the analyte by comparing the colour on the membrane to the colour on an external calibrator, such as a series of coloured plates that are printed on a label. The colour of each plate is associated with a particular concentration of the analyte. The colour on the plate that most closely approximates the colour on the dipstick provides the user with an approximate concentration of the analyte in the test samples. The method has however several drawbacks:
1. Method is time consuming and often requires a number of manipulative steps, for example, the addition and incubation of assay reagents.
2. It is difficult to match the colour of the plates with the colour on the dipstick.

3. Only one sample can be analyzed by one dipstick.
4. The colour on the plates would not fade in proportion to the adverse conditions affecting the colour on the dipstick. Thus, for a particular set of reaction conditions, the comparison of results with the colour on the plates will not give accurate result.

The Immunochromatographic test strip device constitutes an improvement over the simple dipstick. This class of devices has an absorbent strip immobilized with receptor (antibody) near the center of a typically rectangular chromatography medium, e.g. filter paper, membrane and having an end portion for contacting a test solution. The strip having a length and width is capable of conveying fluids in a fluid flow direction generally parallel to the length of the strip. They generally exhibits improved sensitivity in analyte detection relative to that of simple dipstick devices by virtue of the analyte concentrating effect achieved by the flow of sample containing the analyte past an immobilized analyte binding zone. A sample that is suspected of containing the analyte of interest is placed at or near one end of a membrane strip followed by the labeled reagent. The label reagent is an second antibody different from the first antibody yet it also binds with specificity to the analyte, is prepared separately and bound to a detectable marker substance to prepare a marker-second antibody complex. The maker-second antibody complex can be premixed with sample prior to addition to the strip or it can be added substantially simultaneously with the sample or it can be added after sample addition. The mixture is allowed to be carried to the opposite end of the membrane strip by a liquid phase that traverses the membrane strip by capillary action. While traversing the membrane strip, if the sample contains analyte it binds to the receptor (either mobile or stationary phase) and the marker is also captured by the trap yielding a complex of (marker)-(second antibody)-(analyte)-(first antibody). Because the marker is detectable, the presence of the marker can be detected by the naked eye, i. e. by means of colour contrasting with the chromatographic medium. Therefore, a coloured mark or the like will be left by the marker at the site at which the first antibody was affixed and thereby it is possible to easily confirm the presence (or absence) of the analyte. At present, many such in vitro diagnostic kits based on immunochromatography are known and available commercially. The methods are simple, less time consuming however has several drawbacks:
1. The method can only be used for determining the presence or absence of substance of interest or of clinical significance. No quantification of the analyte is possible.
2. The materials and dimensions influence the evenness of the flow of the detecting molecules through the assay. If the flow of liquid is too fast, the detectable molecules are left behind and are not accurately detected by the assay.
3. Only single sample can be analyzed with one assay device.

Flow-through devices, which overcome some of the disadvantages of the Dip-Stick and Immunochromatographic test strip devices were developed using membrane such as nitrocellulose, glass fibre, polyester, cellulose nitrate, polyester, nylon pre-coated with an antigen. These devices utilizes flow of fluid in a direction which is primarily transverse to the plane of the membrane A solution containing the target analyte is drawn through the entire membrane area by capillary action of the absorbent material located adjacent to the membrane. Absorbent material such as cellulose acetate, filter paper, porous polyethylene is capable of absorbing liquid sample in substantially greater amount than that applied during one test. The absorbent body provides a means to collect the sample by providing uniform suction to deliver the sample through the reaction membrane down into the adsorbent body. Thus, the adsorbent body also acts as a reservoir to hold the sample, and various reagents. Samples containing target analyte and reference standards is applied to different areas onto the membrane surface and absorbency of the absorbent will draw the liquid of the sample. Thereafter, signal producing systems capable of generating a detectable visual change on the surface attached to a antibody having binding specificity for the target analyte is drawn through the membrane surface. When the colour producing system is used, antibody conjugated to horseradish peroxidase is exposed to the membrane surface. Subsequent exposure of the membrane to 4-Chloro-1-Naphthol substrate results in deposition of a dark blue dye on the membrane surface due to enzymatic activity. High contrast between the dyed and undyed portions of the membrane surface allows for detection of analyte. Visualization of the intensity of the colour in comparison with known concentration of reference standard gives an idea about the amount of antigen present in the sample. The method is simple and test can be performed under field conditions and results obtained usually under 10 minutes.

Several analytical devices based on Flow-through principle have been developed and described in patents which employs a membrane immunoadsorbent in combination with an absorbent pad. The absorbent body, which constitutes the fluid-receiving zone in these devices, can either be in non-continuous contact with the membrane containing immobilized antibody (U.S. Pat. No. 4,246,339) or in continuous contact with membrane (U.S. Pat. Nos. 4,366,241, 4,446,232, 4,632,901 and 4,727,019). Devices in which absorbent body is not in direct contact with the membrane permit the solution containing sample and/or labeled reagents grater contact with membrane before flow of solution to absorbent body takes place. Such non-continuous contact devices are more efficient at utilization of sample and labeled reagents however they require physical motion by assayist to bring in the flow of liquid. This step can bring about error in the assay. The continuous contact devices are less efficient in utilization of costly-labeled reagents. Thus, a reagent volume substantially greater than the void volume of the membrane is required to ensure that the entire membrane has been contacted with the solution containing reagents.

In both of these types of devices the membrane and absorbent body are contained in a plastic housing having a top member and a bottom member joined together under compression to hold the membrane and absorbent body in place and in contact with each other. In a recent U.S. Pat. No. 5,885,526 to Chu (March 1999), analytical device has been slightly modified by sealing reaction membrane and absorbent body with water insoluble adhesive. Liquid sample is applied to the pad by various techniques, and the sample drawn through the entire membrane area by capillary action of the absorbent pad. The rate and path of fluid flow in assay device has great effect on assay results. A number of devices have been described in the prior art which use surfaces with specifically arranged geometric elements to control the path and the rate of fluid flow. Devices such as are described in U.S. Pat. Nos. 4,426,451 and 5,922,615 utilize an arrangement in which a membrane is placed between smooth surfaced planer sheets of a non-absorbent body in order to contain a fluid within the membrane. Devices such as described in U.S. Pat. Nos. 4,233,029 and 4,310,399 use geometric arrangements of capillary channels to modulate the flow of fluid, such that fluid is directed to flow in regular geometric patterns and at controlled rates. Detection of analyte present in low concentration requires sample concentration. This has been achieved in some analytical devices (U.S. Pat. No. 4,818,677) by having high capacity adsorbent body beneath the reaction membrane, which draws larger volume of sample, added to the top of the membrane. However, because of the non-specific interference, interpretation of the results may not be accurate. The major drawbacks of the developed Flow through devices till date are as follows:
1. The low detection limit of analytical device has limited its application for detection of antigen or antibody, which are present in extremely minute amount.
2. Analytical devices are assembled individually making the manufacturing process complicated and costly.
3. The use of insufficient compression to hold the membrane and absorbent body tends sample to flow laterally during assay leading to inaccuracy in result.
4. Requires application of pressure to force liquid from membrane to absorbent layer.
5. Application of signal amplification step difficult.

OBJECTS OF THE INVENTION

The main object of the present invention is to provide an improved highly cost-effective, easy to manufacture analytical device based on Flow-through principle for performing rapid immunoassays for visual detection of diagnostically important antigen or antibody.

Another object of the invention is to use disposable absorbent body for not only making construction of the device simpler but also for application of elements of signal amplification for attaining ultra high sensitivity.

In yet another object of the invention is to develop a simple assay method with the invented device which without spreading allows always downward flow of sample or costly labeled reagents efficiently, without application of any force to the absorbent body thereby overcoming above described drawbacks of the hitherto known Flow-through devices.

Novelty

The analytical device of the present invention is highly simple in construction compared to hitherto known devices. The materials used for the construction are cheap and except reaction membrane, all are readily available from stationary stores. The absorbent body is not fitted together with reaction membrane using compression or glue during construction. They are provided separately with the device and are discarded after use before proceeding for the next step. These features make the present invented device completely different from hitherto known devices. Additional absorption body are also provided if required by the assay protocol for addition of elements of signal amplification system. The absorbent body used is a simple plane sheet of any conventionally employed absorbent material having liquid absorption capability. No special geometrical arrangements in the absorbent body to control the flow of fluid are required.

The assay procedure developed for performing immunoassay using the invented device is simple and different from the known devices. The absorbent body is first soaked with liquid and assembled to the device in such a way that upper surface of the absorbent body is in intimate contact with the lower surface of the reaction membrane. The pre-wetted absorbent body saturates the void volume of reaction membrane, which thereby does not allow spread of sample or immunoassay reagents. The flow of applied sample or reagent is always downwards and focused without application of any force to the absorbent body thereby costly-labeled reagents can be used efficiently. The void volume of the wetted absorbent body is still sufficient to substantially fill the additional volume of fluid introduced during assay and thereby fulfill the function of fluid receiving zone. The wetted absorbent body controls the flow rate of applied liquid, which prevents spread of fluid and allows higher interaction between the target molecule and immobilized antibody on the reaction membrane, thus increasing the sensitivity. The immunoassays using the invented device are simple and fast, can be qualitative or quantitative.

SUMMARY OF THE INVENTION

The present invention provides a highly cost-effective; easy to manufacture analytical device that can be particularly used for performing immunoassays for detection of analyte within 10 minutes with ultra high sensitivity. The device of the present invention comprises a semi-rigid liquid-impervious support body and a microporous member such as membrane containing multiple immobilized antibody spots attached at the lower surface towards the top breadth side with water-insoluble adhesive over a semi-rigid liquid-impervious body. The device also includes separate sheets of adsorbent body larger in size than membrane, which is not fixed together with membrane in the device during manufacture. The number of sheets of absorption body may be more than one for further addition of elements of signal amplification system after discarding the first absorption body.

DETAILED DESCRIPTION OF THE INVENTION

In the method of present invention, the absorbent body is soaked in fluid and positioned proximal to lower surface of the reaction membrane and pressed so as to be in liquid communication with the reaction membrane. Under these circumstances, the void volume of reactive membrane is saturated and the distance separating the reactive membrane and the absorbent body is such that networks of capillary channels with the absorbent material is formed. The sample or labeled reagent applied to a well-defined area on the membrane passes always downwards without application of any external force. The applied liquid does not spread and are focused within the limited area.

The analytical device and the method of present invention can be adopted for use in many different types of assay. Both conventional and ultrasensitive format may be used depending upon the requirement. Assays are rapid and batch of samples can be analyzed within 4 or 10 minutes. The device finds their greatest use not only with biological specimen but also with industrial, environmental and food samples.

BRIEF DESCRIPTION OF THE DRAWINGS

The device of the invention can be appreciated by the figures, which are schematic drawings and are not drawn to scale.

FIG. 1 is an exploded perspective view of the components of the analytical device.

Figure 1A:
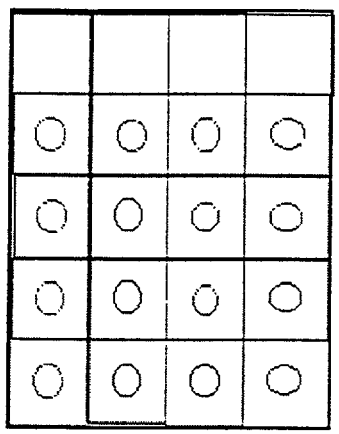
FIG. 1A is a rectangular sheet of reaction membrane

It further comprises a semi-rigid liquid-impervious bottom support layer wherein a portion of lower surface of the said reaction membrane in breadth corner having no immobilized antibody or antigen, is attached to upper surface of support layer by water-insoluble adhesive or tape having glue on both sides. Alternatively, a narrow solid strip of a liquid-impervious body placed in-between reaction membrane and semi-rigid support layer wherein upper surface is attached to a portion of lower surface of the said reaction membrane in breadth corner and lower surface to bottom support layer by water-insoluble adhesive.

It further comprises a body of absorbent material having an upper surface and lower surface, capable of absorbing liquid. It is not fitted together with reaction membrane using compression or adhesives during manufacture. It is provided separately with the analytical device. The upper surface of said absorbent body extends beyond the periphery of said reaction membrane but smaller than the said bottom support layer. The absorbent body is selected from the group consisting of cellulose acetate, filter paper or bathroom tissue paper. The thickness of the said absorbent body may range from about 0.1 to about 8 mm and more. A single analytical device contains more than one disposable absorbent body, which is used for addition of elements of signal amplification reagents.

In the analytical device of the present invention, the size and periphery of the said reaction membrane is much smaller than the said bottom support layer. Further, the size of the reaction membrane is not critical and bigger size can be used in a single device to perform batch of samples. Multiple strips of the reaction membrane can be attached to semi-rigid support layer to perform immunoassay on batch of samples. The reaction membrane comprises nitrocellulose but other variety of semi-permeable membrane materials including nylon, polyvinyledine difloride, and the like may also be used. The average diameter of the membrane is preferably in the range of about 0.22 to about 3 microns and more preferably 0.45 microns. The loose area of the reaction membrane has immobilized thereon the antibody or antigen over entire membrane surface as multiple dots or under certain circumstances it may be desirable to immobilize across the entire membrane surface at uniform concentration. Further, it may be immobilize with more than one specific antibody to the membrane in the same or different areas for simultaneous detection of multiple analyte in a sample with a single assay device.

After immobilization, unused binding sites on nitrocellulose can be blocked with suitable blocking proteins selected from the group consisting of casein, BSA, gelatin and like. Alternatively, for ultrasensitive format vacant binding sites on nitrocellulose membrane are blocked with electron rich blocking proteins such as p-hydoxy-phenylpropionic acid-casein conjugate, p-hydroxy-phenylpropionic acid-gelatin conjugate and like for application of Super-CARD signal amplification.

In a further embodiment of the present invention, the bottom support layer with adequate mechanical strength is used and is selected from the group consisting of polyethylene, plastic and fiberglass. The reaction membranes are attached over bottom support layer using water insoluble adhesive, applied only in the top 4 mm lower portion of the membrane. Alternately, adhesive tape having glue on both sides may also be used to attach membrane over bottom support layer.

In a preferred embodiment of the present invention, assembling of absorbent body with analytical device for performing immunoassay comprises:
(a) Soaking of absorbent body with liquid followed by placing in the analytical device in such a way that upper surface of the absorbent body is in intimate contact with lower surface of the reaction membrane and upper surface over bottom support layer.
(b) The upper surface of the reaction membrane is pressed to remove air entrapped in between lower and upper surface of reaction membrane and absorbent body.
(c) The void volume of reaction membrane is saturated and the distance separating the reactive membrane and the absorbent body is such that networks of capillary channels is formed were the two members are in contact.
(d) The flow of applied sample or reagent is always downwards and focused without application of any force to the absorbent body.
(e) The void volume of the wetted absorbent body is still sufficient to substantially fill the additional volume of fluid introduced during assay.

In the method of the present invention, the absorbent body is soaked in deionized distilled water, buffer and the upper surface of the reaction membrane is pressed with small roller, rim-less small test tubes and like. The pre-wetted absorbent body saturates the void volume of reaction membrane, which thereby does not allow spread of sample or immunoassay reagents. This allows the use of costly labeled reagents efficiently. Various volumes or sample or labeled reagents ranging from 10 µl to 100 µl may be used. The label reagent can be premixed with standard or sample prior to addition to different areas of the membrane in the device or it can be added after standard or sample addition. More than one specific antibody may also be immobilized in the same or different areas for simultaneous detection of multiple analytes in a sample with a single assay device.

After the addition of sample and reagents, absorbent body is discarded and the reaction membrane is washed directly over device with the help of wash bottle. Further, for high sensitivity elements of signal amplification are further added. The signal amplification method like Super-CARD is applied wherein biotinylated tyramine is added directly over reaction membrane in the device. Than a fresh pre-wetted absorbent body is assembled and avidin-peroxidase conjugate is added and washed. This is followed by substrate solution added directly over reaction membrane to produced colour spots within well-defined area. The exposed area of the reaction membrane is sufficiently greater to allow visualization of the intensity of the colour spots. Visual comparison with known concentration in reference standard gives semi-quantitative estimate of the amount of antigen present in the sample Signal amplification step is not necessary for that analyte which is present in high concentration. The assay results can be obtained within 3 to 10 minutes depending upon the format of assay used The assay method using the device can be developed for analyte consisting of antigens, antibodies, haptens, drugs, hormones, macromolecules, toxins, bacteria, viruses, enzymes, tumor markers, environmental pollutants, and nucleic acids.

DESCRIPTION OF THE PREFERED EMBODIMENTS

This invention provides an improved assay device, the construction format of, which is relatively simple, compared to prior art devices, the material cost is lower and the manufacturing process easier. The absorbent body is not fixed permanently with the device but is assembled during the assay. Initially the absorbent body is wetted with fluid like water, buffer like and positioned below reaction membrane, pressed thereby not only substantially filling the required void volume of the reactive membrane but also forming a network of capillary channels with the absorbent body. This ensures the focused downward flow of the applied fluid sample or reagents without any force and also does not allow outward diffusion of costly-labeled reagents. Further, the construction format of the device allows the discarding of used absorbent body with new one thereby permitting the application of signal amplification reagents for improving sensitivity of the assay.

The present invention is useful in assaying for a wide variety of analytes in virtually any type of sample which is liquid, which can be liquefied, or which can be suspended in liquid. The device can be incorporated in test kit and assay method using the device may be developed in conventional or ultrasensitive format depending upon the requirement. The results can be obtained within 3 to 8 minutes depending upon the format used. Analytical device will find their greatest use with biological specimens, such as blood, serum, plasma, urine, saliva and the like. Use will also be found with industrial, environmental and food samples.

The analyte to be detected may be virtually any compound, or other substance, which may be immunologically detected. That is the analyte or portion thereof will be antigenic or haptenic having at least one determinant site, or will be a member of a naturally-occurring binding pair, e.g., carbohydrate and lectin, hormone and receptor, complementary nucleic acids, and the like analyte of particular interest include antigens, antibodies, proteins, carbohydrates, haptens, drugs, hormones, macromolecules, toxins, bacteria, virus, enzymes, tumor markers, nucleic acids, and the like, although other type of substances may also be detected. The detection of aflatoxin B1 a small molecule and human IgG are exemplified in the Examples section, hereinafter.

The analytical device of the present invention comprised of a microporous membrane attached at one end over a semi-rigid liquid-impervious sheet. A water-insoluble adhesive is used to adhere a reaction membrane having an antibody or antigen bound thereon. The second member, an absorbent body, is a separate component larger in size than microporous membrane and is assembled during assay in such a way that they are in intimate contact with each other at their planer surface.

The micro porous membrane of the present invention is intended to separate and immobilize the analyte from the sample as it passes through membrane to the absorbent. The size of the membrane is not critical and bigger size or multiple strips can be used in a single device to perform batch of samples. However, the membrane should have sufficiently large exposed area to allow visualization of each sample or controls on a portion thereof with sufficient excess area so that contrast between the visual signal and the reminder of the membrane may be easily observed. The microporous membrane may be formed from a wide variety of semipermeable membrane materials, including nitrocellulose, polyvinylidene difluoride, nylon, paper and the like. The average pore diameter of the material is usually not critical, although materials having particular pore diameter may be selected for particular assay. However, the porosity of the membrane has a large influence on the flow rate of the liquid and sensitivity of the assay. The larger the pores size of the membrane, the faster the flow rate for a given liquid. As the flow rate increases, the interaction time available between the target molecule in the sample and the antibody immobilized on the reaction membrane decreases, thus decreasing assay sensitivity. For most assays, the porosity of membrane is preferably in the range of about 0.22 to about 3 microns. For most applications, specific binding substances like antibody will be bound to the membrane to facilitate separation of the analyte of interest.

An important preferred embodiment of the invention is the selection of nitrocellulose membrane as the carrier material. This has considerable advantage because it has a natural ability to bind proteins without requiring prior sensitization. Such specific binding substance are usually antibodies capable of binding antigens and haptens, although antigens, hormone receptors, lectin, polysaccharides, nucleic acids, and other natural receptors and legends may also find use. Methods for binding the specific binding substances to the nitrocellulose membrane are well known and amply described in the scientific and patent literature. Unused binding sites on the nitrocellulose can therefore be blocked with blocking proteins such as casein, BSA or gelatin. Electron rich blocking proteins such as p-hydroxyphenylpropionic acid-casein, p-hydroxyphenylpropionic acid-gelatin conjugate are used for blocking vacant sites of the nitrocellulose membrane for ultrasensitive detection of analyte for application of Super-Card signal amplification (*J. Immunological Methods* 227, 31, 1999).

In a preferred embodiment of the present invention the specific binding substances on uniform concentration is immobilized as multiple spots over entire membrane surface or under certain circumstances it may be desirable to bind the substances across the entire membrane surface. The spot approach is preferred, as sample and labeled reagents is concentrated at a single region thereby providing a more distinctive end product signal. In a further particularly preferred embodiment, it may be desirable to sometimes bind more than one specific binding substance to the membrane in the same or different areas, for simultaneous detection of multiple analytes in a sample with a single assay device.

The analytical device of the present invention further comprises a semi-rigid liquid-impervious bottom support layer. The reaction membrane is placed over semi-rigid support layer and one end is attached along breadth side through lower surface. The size of the bottom support layer is much larger than reactive membrane and absorbent body. The bottom support layer is typically comprised of plastic, polyethylene, polyester and like. The selection of proper materials with adequate mechanical strength as the supporting backing for the device is important. Undesirable bending of the assay device may occur if a week backing or inadequate mechanical strength of bottom support layer is used. As has already been noted, typical prior art analytical devices are comprised of top and bottom housing members which are fitted together so as to hold the reaction membrane and absorbent body in place using compression. Because the reaction membrane and absorbent bodies are two independent components of the device and absorbent body is placed only during the assay, there is no need to use fitted or otherwise sealed top and bottom housing members. Bottom support layer supports the reaction membrane during transit and handling of membrane becomes easier during assay. Materials used for bottom support layer could also be used to provide top support layer to cover the membrane, although it may be different.

In yet another aspect of the present invention, multiple microporous membrane strips or in one piece having multiple reactive sites can be attached over solid support layer for analyzing batch of samples. Alternatively, in between the membranes and solid support layer a narrow solid strip typically comprised of any water-impervious material may be attached to provide sufficient space for the absorbent body to be placed beneath the reaction membrane during the assay. The same material as solid support layer having the thickness similar or higher than absorbent material may be used. After the device has been constructed, the top solid support layer may be labeled with a labeling or bar code device to indicate the type of test for which the device is to be used.

In a further embodiment of the inventive device, absorption body is not fitted together with reaction membrane using compression or glue during manufacture. They are provided separately and are discarded after use before proceeding for the next step. Additional absorption body are also provided if required by the assay protocol. In a further embodiment of the analytical device, additional absorption body is used according to above described method for addition of elements of signal amplification system.

The primary requirement of the absorbent solid material is that it is capable of absorbing liquid. Any conventionally employed absorbent material that has liquid absorption capability can be used in the present invention. Useful known materials includes cellulose acetate filters, polyester or other such materials. Layers of commercially available filter paper or bathroom tissue paper can be used. The thickness of the absorbent body (i.e. "side-wall", which is the distance between the upper and lower surfaces of the absorbent material) can vary depending upon the void volume needed for a given immunoassay. Typically, the thickness ranging from about 0.1 mm to about 8 mm, and more. The surface area of the absorbent body is usually greater than that of the reaction membrane but smaller than the bottom support layer. In a preferred embodiment of the present invention absorbent body used is approximately five times the size of the reaction membrane. In the exemplary embodiment, the absorbent body comprises Whatman filter paper No 3.

In the method of the present invention, absorbent body provided with the analytical device is first soaked with excess liquid such as deionized water, buffer and like. The wetted absorbent body is assembled with the analytical device in such a way that upper surface of the absorbent body is in intimate contact with lower surface of the reaction membrane and lower surface is over bottom support layer. The upper surface of the reaction membrane is than pressed with a small roller or rimless test tube in such a way that air entrapped in between lower and upper surface of reaction membrane and absorbent body is removed. Under these circumstances, the void volume of reactive membrane is saturated and the distance separating the reactive membrane and the absorbent body is such that networks of capillary channels is formed were the two members are in contact. The wetted reaction membrane and absorbent body do not allow the fluid of sample and reagents to flow sideways across the reaction membrane into the absorbent body. In the method of the present invention, the flow of the sample or reagent is always downwards and focused without application of any force to the absorbent body thereby costly-labeled reagents can be used efficiently. The void volume of the wetted absorbent body is still sufficient to substantially fill the additional volume of fluid introduced during assay and thereby fulfill the function of fluid receiving zone. The wetting of the absorbent body has large influence on the flow rate of the liquid and sensitivity of the assay. Excess wetting of the absorbent body reduces the flow rate thereby allowing the fluid to spread. If the wetting is less, the flow rate increases, which decreases the interaction between the target molecule in the sample and the immobilized antibody on the reaction membrane, thus decreasing the sensitivity.

The immunoassays that use the analytical device of the present invention can be very simple and fast, can be qualitative or quantitative. Many different types of immunoassays, known in the art can be performed using these analytical devices. The immunoassay format depends on the type of analyte to be detected.

Various detection reagents can be used to further simplify and improve assay sensitivity. Direct labels such as gold sols and dye solutions can also be used. Again methods are already known in the art. Assay method using the device may be in conventional or ultrasensitive format depending upon the requirement. The single absorbent body is used for addition of standards or sample and label reagent. The label reagent can be premixed with standard or sample prior to addition to different areas of the membrane in the device or it can be added after standard or sample addition. In ultrasensitive format the used absorbent body is removed after the convention immunoassay and membrane surface in the analytical device is directly washed. This is followed by addition of signal amplification reagent directly and or using a new absorbent body provided with the device. For example, for Super-CARD signal amplification method, a solution of biotinylated tyramine solution is added directly over membrane without absorbent body and washed with washing buffer. Then a new absorbent body is assembled according to the method described above and Avidin-peroxidase is added over reaction membrane. Visual comparison of the intensity of the colour of the spots with those of known concentration in reference standard gives semi-quantitative estimate of the amount of antigen present in the sample.

All cited references are incorporated herein by references in their entireties. The following examples and drawings are for illustrative purpose only and are not to be construed as limiting the scope of the invention in any manner.

EXAMPLE 1

Conventional Assay for Aflatoxin $B_1$ Using Present Invention

A. Antibody to Aflatoxin $B_1$. The immunogen, aflatoxin $B_1$-O-Carboxymethyloxime-BSA conjugate was prepared according to a standard method using stoichiometry of 20:1 aflatoxin $B_1$ derivative:protein. The immunogen was injected into rabbits together with Freund's adjuvant and a highly specific antiserum was obtained. The gamma globulin fraction of this antiserum was purified by repeated precipitation with ammonium sulfate followed by dialysis against phosphate buffer saline. It was than passed through a BSA-Sepharose 4B immunosorbent column to remove anti-BSA antibody.

Figure 1B:
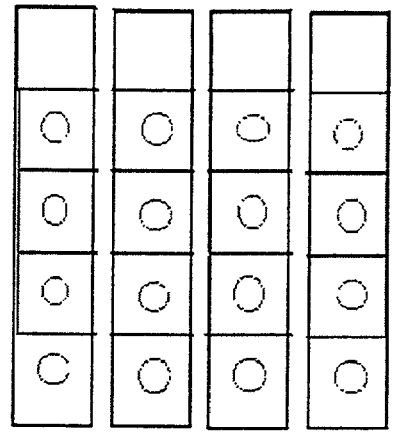
FIG. 1B are strips of reaction membrane.
Figure 1C:
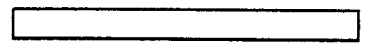
FIG. 1C is a narrow solid strip of liquid-impervious body.

B. Test Device Preparation. Schleicher & Schuell nitrocellulose membrane having pore size of 0.45 micron is cut to a rectangular piece (14 mm. times. 70 mm) and marked with pencil 14×14 mm (FIG. 1A). The membrane can also be cut in strips (14×70 mm) and marked with pencil 14×14 mm (FIG. 1B). The membrane is then soaked in blotting buffer (Tris-HCl, 20 mM, pH 8.0 containing 0.9% NaCl) for 5 min with gentle shaking. The strips were than semi-dried and spotted with dispenser (Hamilton) at multiple sites at a distance of 1.4 cm with 5 µl of a rabbit antibody to aflatoxin $B_1$ diluted 100-fold in Tris-buffered saline (0.05M, pH 8.0). The top 14 mm square in the breadth side of the rectangular membrane was not spotted for attachment to semi-rigid material. After drying the membrane at room temperature for 15 min it was further dried by incubating at 37° C. for 30 min. The vacant sites of the membrane strip were blocked by incubating with 0.4% casein in carbonate-bicarbonate buffer (0.05M, pH 9.6) for 1 hr. at 22 to 26° C. with gentle shaking. The membrane strips were than washed three times with washing buffer (Tris-HCl buffer, 20 mM, pH 8.0, containing 29 g/l NaCl and 0.5% Tween 20). Finally membranes were rinsed with 0.1% thimerosal and than dried at room temperature for 15 min followed by at 37° C. for 30 min. These membranes can be stored in a desecrator till use.

Figure 1D:
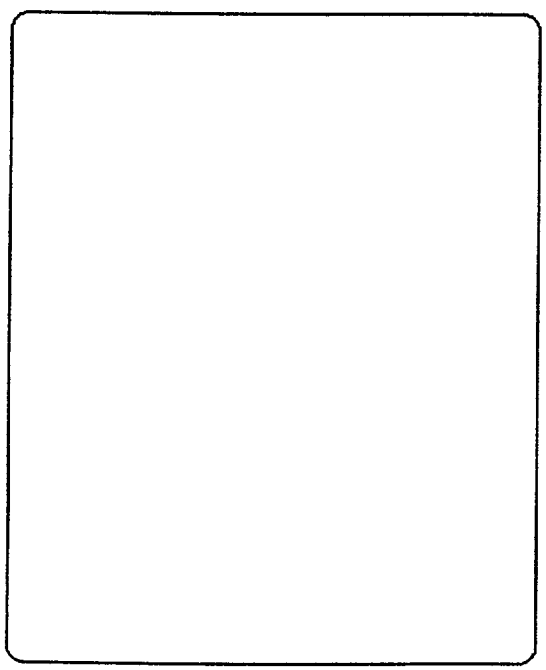
FIG. 1D is a semi-rigid liquid-impervious a bottom support layer of analytical device.
Figure 2A:
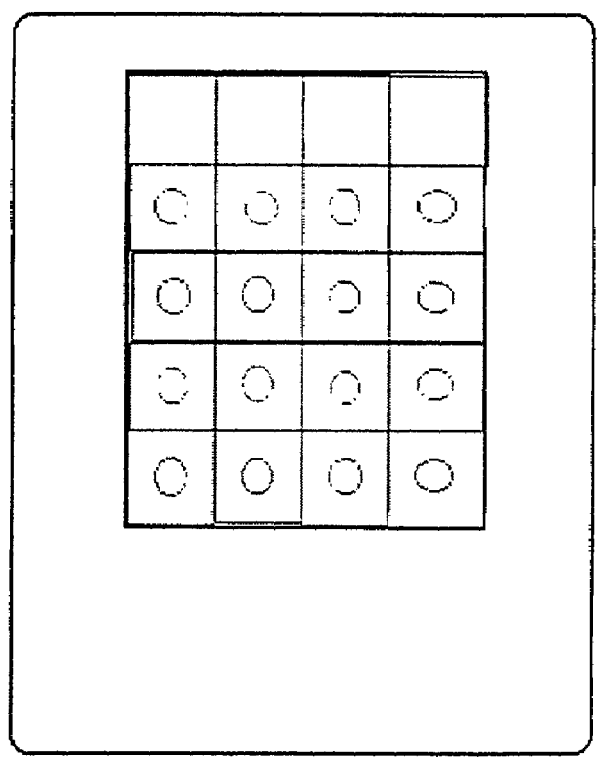
FIGS. 2 (A and B) is a perspective view of the analytical device according to the present invention.
Figure 2B:
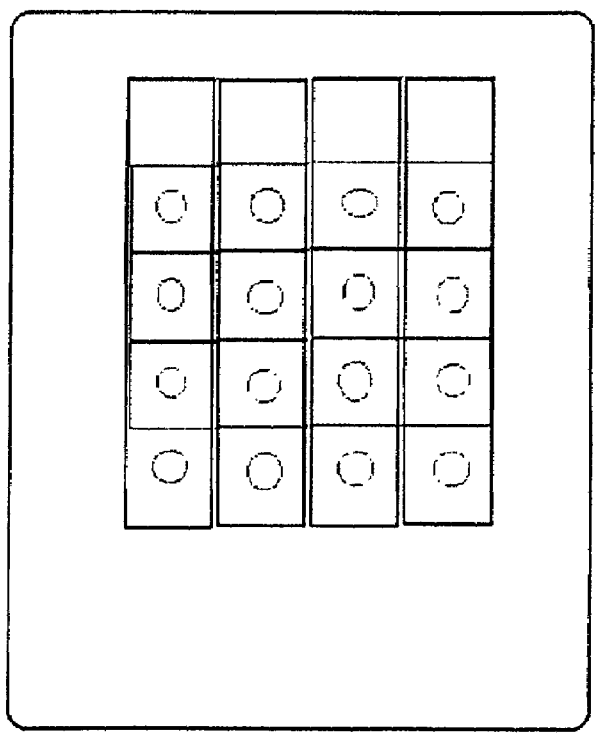

To assemble the test device, a semi-rigid material such as polyethylene sheet (140×120 mm) with thickness about 0.005 to 0.030 inches was taken (FIG. 1D). In the unspotted corner top of the membrane, a 4 mm layer of water-insoluble adhesive is applied. The membrane is than placed at a distance of 15 mm from the top in the breadth wise over rectangular polyethylene sheet (FIG. 2). Adhesive tape having glue on the both sides may also be used to attach membrane.

Figure 3A:
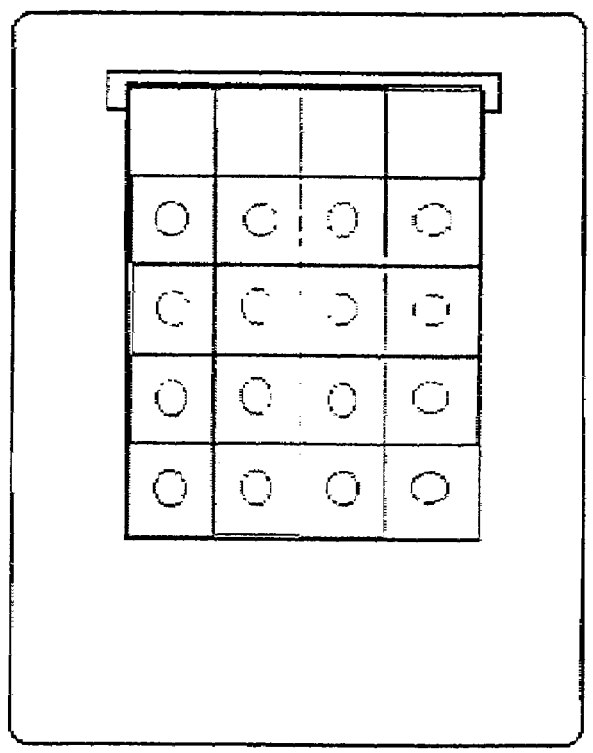
FIGS. 3 (A and B) is a perspective view of the alternative analytical device according to the present invention.
Figure 3B:
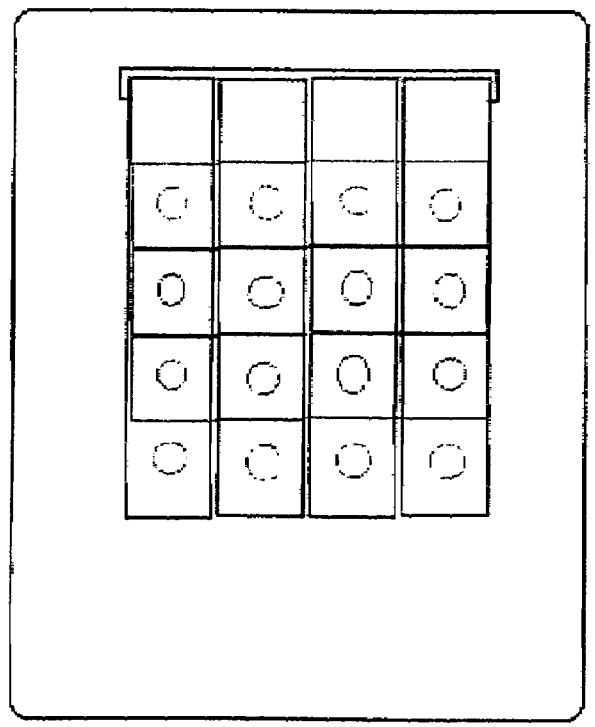

Alternatively, a narrow solid strip of a liquid-impervious body placed in-between membrane and semi-rigid support layer may be used wherein upper surface is attached to a portion of lower surface of the said membrane in breadth corner and lower surface to bottom support layer by water-insoluble adhesive (FIG. 3).

Figure 1E:
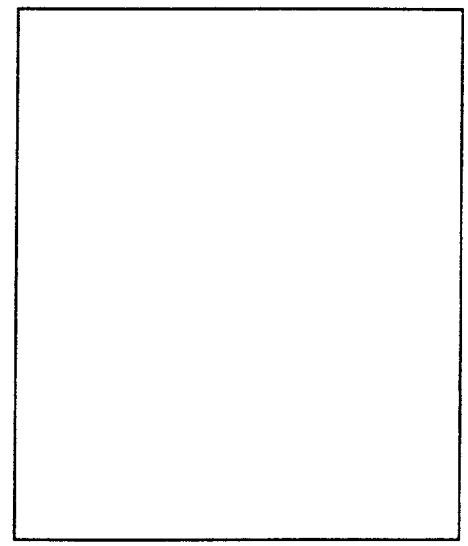
FIG. 1E is an absorbent body, which is not attached to analytical device during manufacture.

One rectangular piece of filter paper (Whatman No. 3) measuring 125×110 mm. (FIG. 1E) is cut from the filter paper sheet for use during the assay. This analytical device can be stored in a desecrator.

C. Enzyme Conjugate Preparation. Aflatoxin $B_1$-O-carboxymethyl oxime-Horseradish peroxidase conjugate was prepared according to a standard method using stoichiometry of 5:1 aflatoxin $B_1$ derivative:peroxidase. It was purified by dialysis followed by chromatography on Sephadex G-50. After the addition of BSA, 20 g/l, working solution of enzyme conjugate (1:100) was prepared in phosphate buffer (0.05M, pH 7.6 containing per liter 0.9% NaCl, 0.4% BSA and 0.01% thimerosal).

D. Sample Preparation. The infected seeds were soaked in water for 1 hr at 22 to 26° C. and dried on filter paper. The seeds (1 gm) was homogenized in methanol (10 ml) and centrifuged at 10, 000 rpm for 15 min. The supernatant was used in the assay by diluting 1000-fold with assay buffer (Tris-HCl buffer, 0.05M, pH 8.0 containing 0.9% NaCl, 0.02% BSA and 0.01% thimerosal).

E. Aflatoxin $B_1$ Standards. Aflatoxin $B_1$ stock standard solution (0.25 mg/ml in acetonitrile) was stored in −20° C. and working standard solution (0, 25 pg, 50 pg, and 100 pg/25 μl) was prepared by diluting with assay buffer.

F. Substrate solution. 3, 3'-Diaminobenzidine (15 mg) and Immidazole (201 mg) was dissolved in 30 ml of Tris-HCl buffer (0.05M, pH 8.0) and 0.001% $H_2O_2$ was added. The solution was stored in the dark till use.

G. Procedure for Testing the Presence of Aflatoxin $B_1$ in Samples (Two-step). Rectangular piece of filter paper (FIG. 1E) was wetted with distilled water and placed in between membrane and polyethylene sheet of the Test device (FIG. 4 or 5). Air entrapped in-between membrane and filter paper was removed by rotating a rimless glass tube over membrane strip. Standard or sample (25 μl) was added slowly over different antibody spotted area of the membrane. The solution is immediately absorbed due to capillary action created by filter paper. Now, over each spotted area where standard or samples have been added, 25 μl of $AFB_1$-HRP conjugate (1:1000) in assay buffer was added. Filter paper is removed and membrane is thoroughly washed with wash buffer. Substrate solution (DAB) is added over membrane and incubated for 1 min and washed with water. Visualization of the intensity of the colour spots in comparison with known concentration in reference standard gives an idea about the amount of antigen present in the sample. The assay sensitivity is measured to be 20 pg/25 μl aflatoxin $B_1$.

EXAMPLE 2

The same procedures as Example 1(A), 1(B), 1(C), 1(D), 1(E), 1(F) is followed except that in 1(F) standard 50, 100 and 200 pg/25 μl were used. Standard or samples is mixed in equal proportion with $AFB_1$-HRP conjugate (1:500) and 25 μl was added over $AFB_1$ antibody spotted area. The results obtained in this One-step method were almost similar to that of Two-step.

EXAMPLE 3

The same procedure as Example 2 is followed except that standard or samples is mixed in equal proportions with 1000-fold $AFB_1$-HRP conjugate and 25 μl of each mixture were added twice over $AFB_1$ antibody spotted area. The results obtained in this method were almost similar to those obtained in Examples 1 and 2.

EXAMPLE 4

Ultrasensitive Assay for Aflatoxin $B_1$ Using the Present Invention

A. Preparation of 3-(p-hydroxyphenyl) propionic acid-casein conjugate (p-OH-PPA-casein). Casein (1 gram) dissolved in 30 ml of sodium bicarbonate (150 mmol/l) was added dropwise under stirring 300 mg of p-OH-PPA-N-hydoxysuccinimide dissolved in dry dimethylformamide. The reaction mixtures were stirred continuously at room temperature for 3 hours and than dialyzed extensively against distilled water and subsequently against phosphate buffer (20 mmol/l, pH 7.6). The p-OH-PPA-casein conjugate obtained were centrifuged to remove the slight turbidity and then lyophilized.

B. Preparation of biotinylated tyramine. A solution of biotin (100 mg) in a mixture of dry dimethylformamide and dimethylsulfoxide (1:2.3) was treated with N-hydroxysuccinimide (70 mg) and dicyclohexylcarbodiimide (120 mg) overnight at 4° C. The activated ester solution was filtered to remove urea and added to a solution of tyramine hydrochloride (60 mg) in 1 ml of dimethylformamide. The reaction mixture was stirred overnight in the presence of powered solid sodium carbonate and filtered. The resulting solution (3 ml) was aliquoted and stored at −20° C. A working solution (200 µmol/l in distilled water) was prepared and stored at 4° C. In assay biotinylated tyramine working solution was diluted 2-fold with borate buffer (0.2 M, pH 8.0 containing 0.008% $H_2O_2$) and used directly.

C. Test Device Preparation. Schleicher & Schuell nitrocellulose membrane having pore size of 0.45 micron is cut to a rectangular piece (14 mm. times. 70 mm) and marked with pencil 14×14 mm (FIG. 1A). The membrane can also be cut in strips (14×70 mm) and marked with pencil at a distance of 14 mm (FIG. 1B). The membrane is soaked in blotting buffer (Tris-HCl, 20 mM, pH 8.0 containing 0.9% NaCl) for 5 min with gentle shaking. The strips were than semi-dried and spotted with dispenser (Hamilton) at multiple sites at a middle of 14 mm square with 5 µl of a rabbit antibody to aflatoxin $B_1$ diluted 2500-fold in Tris-buffered saline (0.05M, pH 8.0) supplemented with 25 µg/ml BSA. The top 14 mm square in the breadth side of the rectangular membrane was not spotted for attachment to semi-rigid material. After drying the membrane at room temperature for 15 min it was further dried by incubating at 37° C. for 30 min. The vacant sites of the membrane strip were blocked by incubating with 0.2% p-OH-PPA-casein in carbonate-bicarbonate buffer (0.05M, pH 9.6) for 1 hr. at 22 to 26° C. with gentle shaking. The membrane strips were than washed three times with washing buffer (Tris-HCl buffer, 20 mM, pH 8.0, containing 29 g/l NaCl and 0.5% Tween 20). Finally membranes were rinsed with 0.1% thimerosal and than dried at room temperature for 15 min followed by at 37° C. for 30 min. These membranes can be stored in a desecrator till use.

To assemble the test device, a semi-rigid material such as polyethylene sheet (140×120 mm) with thickness about 0.005 to 0.030 inches was taken (FIG. 1D). In the unspotted corner top of the membrane, a 4 mm layer of water-insoluble adhesive is applied. The membrane is than placed at a distance of 15 mm from the top over rectangular polyethylene sheet (FIG. 2). Adhesive tape having glue on the both sides may also be used to attach membrane.

Alternatively, a narrow solid strip of a liquid-impervious body placed in-between membrane and semi-rigid support layer may be used wherein upper surface is attached to a portion of lower surface of the said membrane in breadth corner and lower surface to bottom support layer by water-insoluble adhesive (FIG. 3).

One rectangular piece of filter paper (Whatman No. 3) measuring 125×110 mm. (FIG. 1E) is cut from the filter paper sheet for use during the assay. This analytical device can be stored in a desecrator.

D. Sample Preparation. The infected seeds were soaked in water for 1 hr at 22 to 26° C. and dried on filter paper. The seeds (1 gm) was homogenized in methanol (10 ml) and centrifuged at 10, 000 rpm for 15 min. The supernatant was used in the assay by diluting 20,000-fold with assay buffer (Tris-HCl buffer, 0.05M, pH 8.0 containing 0.9% NaCl, 0.02% BSA and 0.01% thimerosal).

E. Aflatoxin $B_1$ Standards. Aflatoxin $B_1$ stock standard solution (0.25 mg/ml in acetonitrile) was stored in −20° C. and working standard solution (0, 1 pg, 5 pg, and 10 pg/25 µl) was prepared by diluting with assay buffer.

F. Substrate solution. 4-chloro-1-naphthol (15 mg) was dissolved in 6 ml methanol and diluted to 30 ml with Tris-HCl buffer (0.1 M, pH 8.0). The solution was stored in the dark after addition of 0.001% $H_2O_2$.

Figure 4A:
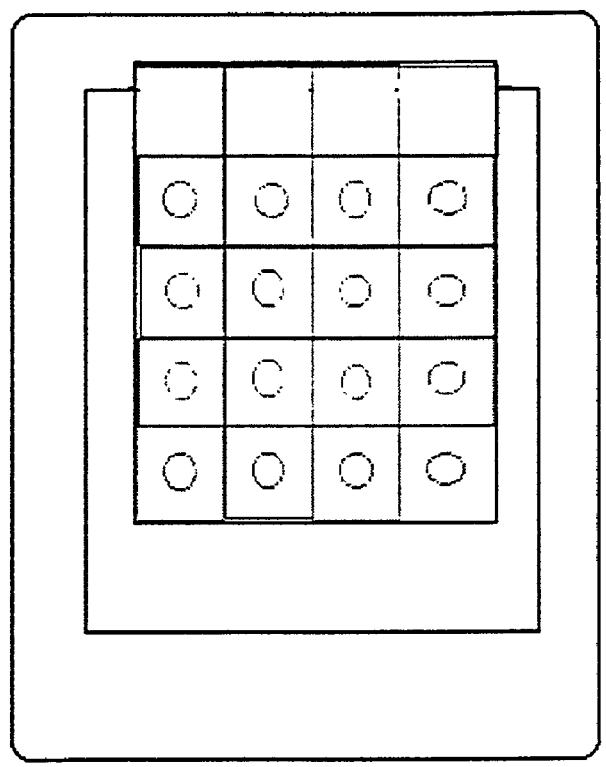
FIGS. 4 (A and B) is a perspective view of analytical device for performing an immunoassay in accordance with the present invention FIGS. 5 (A and B) is a perspective view of the alternative analytical device for performing an immunoassay in accordance with the present invention Accordingly, the present invention provides an analytical device for performing immunoassay for the detection of analyte in a liquid sample wherein a reaction membrane which is liquid-permeable and porous and having an upper and lower surface, an exposed area of the said upper surface having immobilized therein an antibody or antigen capable of binding to the target analyte said immobilized antibody or antigen being concentrated in a multiple spotted region of said upper surface.
Figure 4B:
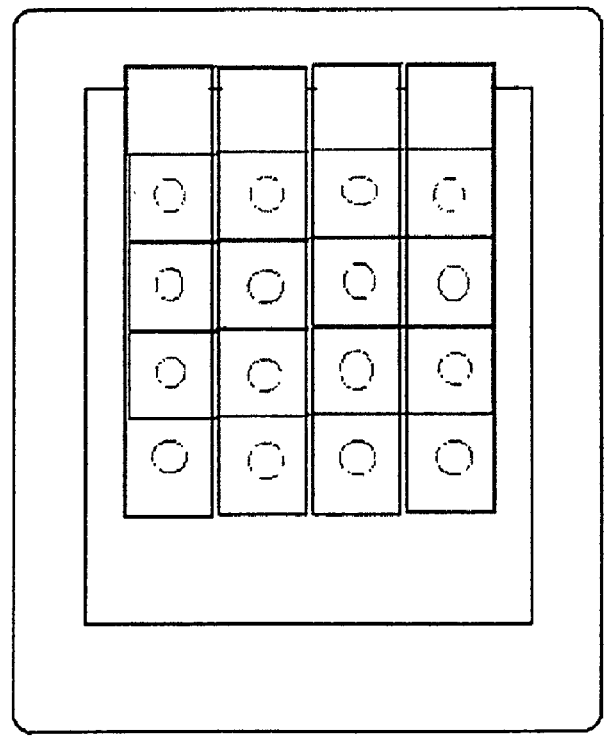
Figure 5A:
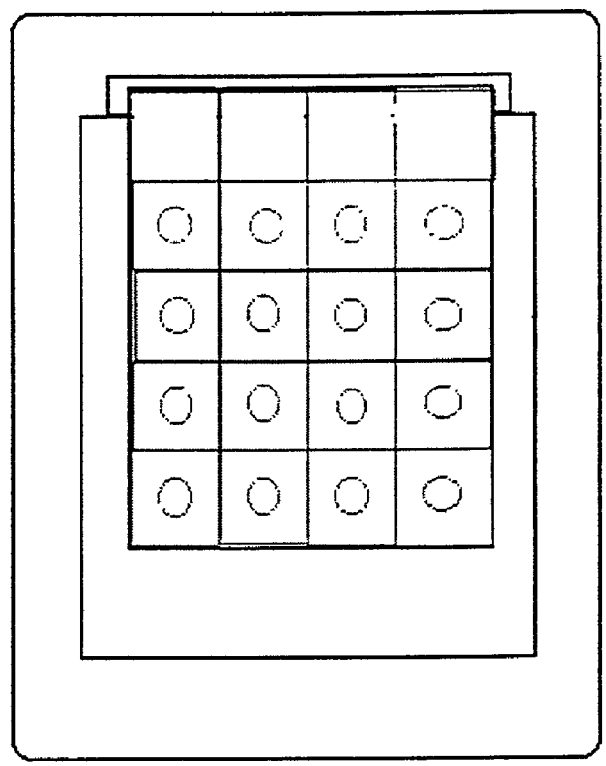
Figure 5B:
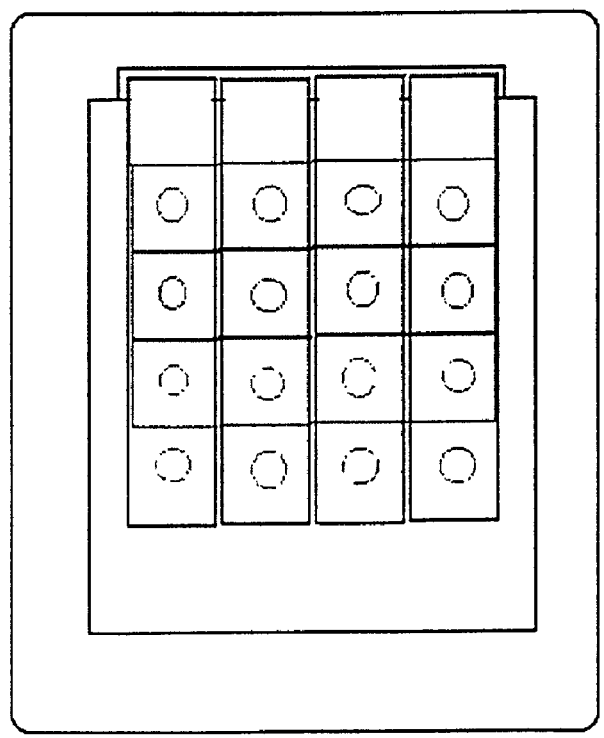

G. Procedure for Testing the Presence of Aflatoxin $B_1$ in Samples (Two-step). Rectangular piece of filter paper was wetted with distilled water and placed in between membrane and polyethylene sheet of the Test device (FIGS. 4 or 5). Air entrapped in-between membrane and filter paper was removed by rotating a rimless glass tube over membrane strip. Standard or sample (25 µl) was added slowly over different antibody spotted area of the membrane. The solution is immediately absorbed due to capillary action created by filter paper. Now, over each spotted area where standard or samples have been added, 25 µl of $AFB_1$-HRP conjugate (1:20,000) in assay buffer was added. Filter paper is removed and membrane is thoroughly washed with washing buffer. For amplification, membranes were treated with biotinylated tyramine solution at room temperature for 2 min. Membranes were again washed with washing buffer. Then again rectangular piece of filter paper was wetted with distilled water and placed in between membrane and polyethylene sheet of the Test device. Air entrapped in-between membrane and filter paper was removed by rotating a rimless glass tube over membrane strip. Avidin-HRP conjugate (purchased from Sigma, St. Louis, USA) was diluted 500-fold with assay buffer and 25 µl was added over each anti-$AFB_1$ spotted area. Filter paper is removed and membrane is thoroughly washed with wash buffer. Substrate solution (4CN) is added over membrane and incubated for 2 min and washed with water. Visualization of the intensity of the colour spots in comparison with known concentration in reference standard gives an idea about the amount of antigen present in the sample. The assay sensitivity is measured to be 0.5 pg/25 µl aflatoxin $B_1$.

EXAMPLE 5

The same procedures as Example 4(A), 4(B), 4(C), 4(D), 4(E), 4(F). 4(G) is followed except that in 4(G) standard 2, 10 and 20 pg/25 µl was used. Standard or samples is mixed in equal proportion with $AFB_1$-HRP conjugate (1:10,000) and 25 µl was added over $AFB_1$ antibody spotted area. The results obtained in this One-step method showed slightly higher sensitivity than that of Two-step method.

EXAMPLE 6

Ultrasensitive Assay for Human IgG Using the Present Invention

Analytical device was assembled as described in Example 4 except that membrane was spotted with 5 µl of 1:100 Protein A solution (Stock 0.4 mg/ml) in sodium phosphate buffer (10 mM, pH 7.6 containing 137 mM NaCl, 0.02% KCl) with Dilutor (Hamilton). The reagent p-OH-PPA-casein, biotinylated tyramine and substrate were same as described in Example 4.

A. Human IgG standards. Human IgG stock standard solution (0.25 mg/ml in assay buffer) was diluted with assay buffer to prepare working standards: 62.5, 125, 250, 500 and 1000 ng/25 µl.

B. Assay procedure. The same assay procedure as described in Example 4G is followed. Human IgG standards (25 µl) was added to the reaction membrane and allowed to completely absorb. Then, 25 µl of Protein A-HRP conjugate (Sigma, USA) diluted 1:8000 in Tris-HCl buffer (50 mM, pH 8.0 containing 0.4% BSA) was added and allowed to completely absorb. Washing buffer (1 ml) was added to the reaction membrane and then washed with washing buffer to remove unbound reagents from the membrane. Now the signal amplification reagents are added as described in Example 4G. A sample containing unknown quantities of IgG was determined (semi-quantitative) by comparing to the standard curve. This demonstrates that the analytical device can be used to detect low concentration of IgG.

EXAMPLE 7

Analytical device was assembled as described in Example 6. Serial dilution of normal human serum (1:500 to 1:32,000) was made in sodium phosphate buffer saline containing 0.4% BSA. A 25 µl of each dilution of human serum was added to the reaction membrane and allowed to completely absorb. A 25 µl of the Protein A-HRP conjugate solution (1:8000) described in Example 6 was added to the reaction membrane and allowed to completely absorb. The remainder of the assay is similar to that described in Example 6. At the end of the assay, a purple spot was visible on the analytical device at a 1:16,000 dilution of normal human serum, indicating that IgG was present and detectable at that dilution using the analytical device and the above assay procedures.

ADVANTAGES i. Analytical device is highly cost-effective and easy to manufacture.
ii. The materials used for the construction are cheap and except reaction membrane, all are readily available from stationary stores.
iii. Absorbent body is not fitted together with reaction membrane using compression or glue during manufacture and are provided separately.
iv. Absorbent body is assembled during the assay and is discarded after use before proceeding for the next step.
v. Additional absorbent body are also provided if required by the assay protocol for addition of elements of signal amplification system.
vi. The method developed for performing immunoassay using the device is simple and allows the flow of the sample and costly-labeled reagents always downwards and focussed without application of any force to the absorbent body.
vii. The method is useful in assaying wide variety of analytes.
viii. Assays are non-instrumental and can be used under field conditions.
ix. Visualization of the intensity of the colour spots in comparison with known concentration in reference standard gives an idea about the amount of antigen present in the sample.
x. Sensitivity of the method can be increased by signal amplification.
xi. Results can be obtained within 3 to 8 minutes depending on the immunoassay format used.
xii. Batch of samples can be analyzed.
xiii. Direct labels such as gold sols and dye solutions can be used.
xiv. Skilled personal not required to perform the assay.
xv. Quantitative results are possible by using Gel-Documentation system.

The invention claimed is:

1. An analytical device for performing an immunoassay for the detection of a target analyte in a liquid sample comprising:
   (a) a liquid-permeable porous reaction membrane having an upper and a lower surface, an exposed area of the upper surface having immobilized thereupon an antibody or antigen capable of binding to the target analyte, wherein said immobilized antibody or antigen being concentrated in multiple spotted regions of the said upper surface, and a portion of the lower surface of the reaction membrane in breadth corner has no immobilized antigen or antibody,
   (b) a semi-rigid liquid impervious bottom support layer attached to the lower surface of the reaction membrane at the breadth corner by water insoluble adhesive or tape having glue on both sides,
   (c) a body of absorbent material having an upper surface and a lower surface, capable of absorbing liquid, wherein the body of absorbent material is provided separately from the analytical device and in use, the absorbent material is pre-wetted with a liquid and is placed between and in contact with the reaction membrane, which is above the body of the absorbent material, and the bottom support layer, which is below the body of the absorbent material, and
   (d) the body of absorbent material is capable of absorbing liquid and is larger in size than the reaction membrane.

2. The analytical device as claimed in claim 1, wherein the size and periphery of the reaction membrane is smaller than the bottom support layer.

3. The analytical device as claimed in claim 1, wherein the upper surface of the absorbent body extends beyond the periphery of the reaction membrane but is smaller than the bottom support layer.

4. The analytical device as claimed in claim 1, wherein the absorbent body is not fitted together with the reaction membrane using compression or adhesives during manufacture.

5. The analytical device as claimed in claim 1, wherein the narrow solid-strip thickness is similar or higher than the absorbent body.

6. The analytical device as claimed in claim 1, wherein multiple strips of the reaction membrane can be attached to semi-rigid support layer to perform the immunoassay on a batch of samples.

7. The analytical device as claimed in claim 1, wherein the reaction membrane is selected from nitrocellulose, semi-permeable membrane materials, nylon, and polyvinyledine difloride.

8. The analytical device as claimed in claim 1, wherein the reaction member is circular and the average diameter of the reaction membrane is in the range of about 0.22 to about 3 microns.

9. The analytical device as claimed in claim 1, wherein more than one specific antibody is immobilized to the membrane in the same or different areas for simultaneous detection of multiple analyte in a sample.

10. The analytical device as claimed in claim 1, wherein the reaction membrane is nitrocellulose and unused binding sites on the nitrocellulose membrane are blocked with the blocking protein.

11. The analytical device as claimed in claim 1, wherein the electron rich blocking proteins are p-hydoxy-phenylpropionic acid-casein conjugate or p-hydroxy-phenylpropionic acid-gelatin conjugate.

12. The analytical device as claimed in claim 1, wherein the bottom support layer is selected from the group consisting of polyethylene, plastic and fiberglass.

13. The analytical device as claimed in claim 1, wherein the reaction membrane is attached over the bottom support layer using a water insoluble adhesive applied in the top 4 mm lower portion of the membrane.

14. The analytical device as claimed in claim 1, wherein an adhesive tape having glue on both sides may also be used to attach the membrane over the bottom support layer.

15. The analytical device as claimed in claim 1, wherein the absorbent body is selected from the group consisting of cellulose acetate, filter paper, bathroom tissue paper and a suitable absorbent material.

16. The analytical device as claimed in claim 1, wherein the thickness of the absorbent body ranges from about 0.1 to 8.0 mm.

17. The analytical device as claimed in claim 1, further comprising more than one disposable absorbent body, wherein in use, the absorbent material pre-wetted with a liquid that is placed between and in contact with the reaction membrane, which is above the body of absorbent material and the bottom support layer, which is below the body of the absorbent material.

18. The analytical device as claimed in claim 8, wherein the diameter of the reaction membrane is about 0.45 microns.

* * * * *